(12) United States Patent
Soerens et al.

(10) Patent No.: US 8,506,978 B2
(45) Date of Patent: Aug. 13, 2013

(54) BACTERIOSTATIC TISSUE PRODUCT

(75) Inventors: Dave Allen Soerens, Neenah, WI (US); Cathleen Mae Uttecht, Menasha, WI (US); Bao Trong Do, Decatur, GA (US); SooYeon Oh, Seoul (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 12/980,037

(22) Filed: Dec. 28, 2010

(65) Prior Publication Data
US 2012/0164206 A1 Jun. 28, 2012

(51) Int. Cl.
*A01N 25/34* (2006.01)
*A01N 33/02* (2006.01)
*B31F 1/12* (2006.01)
*A01P 1/00* (2006.01)
*D21H 27/02* (2006.01)

(52) U.S. Cl.
USPC ........ 424/414; 424/78.08; 162/112; 428/152; 264/282

(58) Field of Classification Search
USPC ................. 424/414, 327; 442/414, 327, 102, 442/459, 59
See application file for complete search history.

(56) References Cited

U.S. PATENT DOCUMENTS

| | | |
|---|---|---|
| 3,296,065 A | 1/1967 | O'Brien et al. |
| 3,305,392 A | 2/1967 | Britt |
| 3,677,888 A | 7/1972 | Economou |
| 3,700,623 A | 10/1972 | Keim |
| 3,840,504 A | 10/1974 | Keim |
| 4,007,113 A | 2/1977 | Ostreicher |
| 4,063,995 A | 12/1977 | Grossman |
| 4,347,339 A | 8/1982 | Boevink et al. |
| 4,518,610 A | 5/1985 | Umekawa et al. |
| 5,061,346 A | 10/1991 | Taggart et al. |
| 5,098,520 A | 3/1992 | Begala |
| 5,223,096 A | 6/1993 | Phan et al. |
| 5,240,562 A | 8/1993 | Phan et al. |
| 5,262,007 A | 11/1993 | Phan et al. |
| 5,266,164 A | 11/1993 | Novak et al. |
| 5,275,698 A | 1/1994 | Dasgupta et al. |
| 5,312,522 A | 5/1994 | Van Phan et al. |
| 5,334,286 A | 8/1994 | Van Phan et al. |
| 5,354,424 A | 10/1994 | Rha et al. |
| 5,427,696 A | 6/1995 | Phan et al. |
| 5,437,766 A | 8/1995 | Van Phan et al. |
| 5,538,595 A | 7/1996 | Trokhan et al. |
| 5,558,873 A | 9/1996 | Funk et al. |
| 5,624,532 A | 4/1997 | Trokhan et al. |
| 5,635,028 A | 6/1997 | Vinson et al. |
| 5,783,996 A | 7/1998 | Muszynski |
| 5,846,380 A | 12/1998 | Van Phan et al. |
| 5,958,187 A | 9/1999 | Bhat et al. |
| 6,030,443 A | 2/2000 | Bock et al. |
| 6,083,586 A | 7/2000 | Andersen et al. |
| 6,117,491 A | 9/2000 | Rutanen et al. |
| 6,123,996 A | 9/2000 | Larsson et al. |
| 6,207,734 B1 | 3/2001 | Vinson et al. |
| 6,328,849 B1 | 12/2001 | Dwiggins et al. |
| 6,338,855 B1 * | 1/2002 | Albacarys et al. ............ 424/409 |
| 6,582,559 B2 | 6/2003 | Thornton et al. |
| 6,596,126 B1 | 7/2003 | Shannon et al. |
| 6,783,846 B2 | 8/2004 | Larsson et al. |
| 6,797,856 B1 | 9/2004 | Kolb et al. |
| 6,911,114 B2 | 6/2005 | Lindsay et al. |
| 7,744,722 B1 | 6/2010 | Tucker et al. |
| 2001/0040136 A1 | 11/2001 | Wei et al. |
| 2002/0026993 A1 | 3/2002 | Thornton et al. |
| 2003/0024667 A1 | 2/2003 | Wallenius et al. |
| 2004/0058606 A1 * | 3/2004 | Branham et al. .............. 442/327 |
| 2004/0062907 A1 * | 4/2004 | Lindsay et al. ................ 428/113 |
| 2004/0129395 A1 | 7/2004 | Rehders et al. |
| 2005/0006040 A1 | 1/2005 | Boettcher |
| 2005/0230069 A1 | 10/2005 | Hilbig et al. |
| 2007/0000630 A1 | 1/2007 | Hassler et al. |
| 2007/0284069 A1 | 12/2007 | Dyer et al. |
| 2009/0181157 A1 | 7/2009 | Toreki et al. |

FOREIGN PATENT DOCUMENTS

| | | |
|---|---|---|
| CA | 2 280 082 C | 8/2006 |
| EP | 0 470 871 A1 | 2/1992 |
| EP | 0 964 955 A1 | 12/1999 |
| EP | 1 106 236 A1 | 6/2001 |
| EP | 2 199 046 A1 | 6/2010 |
| WO | WO 2008/063068 A1 | 5/2008 |
| WO | WO 2011/085499 * | 1/2011 |

* cited by examiner

*Primary Examiner* — Fereydoun G Sajjadi
*Assistant Examiner* — Anna Falkowitz
(74) *Attorney, Agent, or Firm* — Michael J. Sullivan

(57) ABSTRACT

A tissue product comprising an additive composition onto at least the surface of a fibrous article in order to increase the surface potential of the article, while retaining or improving manufacturing efficiency is disclosed. The additive composition comprises a bacteriostatic component and more preferably a water-soluble adhesive component and a bacteriostatic component. In some aspects, the additive may also contain additional water-soluble modifier components. Tissue products according to the present disclosure can attract and trap negatively charged matter, such as bacteria, into the tissue web. As such, tissue products can pickup bacteria from a surface and substantially hold the bacteria in the sheet to help prevent spreading bacteria to other surfaces.

28 Claims, 3 Drawing Sheets

BACTERIOSTATIC TISSUE PRODUCT

FIELD OF THE INVENTION

This application relates generally to a tissue product containing a bacteriostatic composition capable of capturing and trapping negatively charged matter, such as bacteria. More specifically this application relates to a creped tissue sheet wherein a bacteriostatic creping additive is applied to at least one side of the sheet resulting in a tissue sheet having a surface charge of at least about 2000 mV.

BACKGROUND

A myriad of different types of fibrous webs are commercially available in today's marketplace. These fibrous webs can contain chemicals designed with a particular use in mind. For example, fibrous webs can be used to deliver chemicals designed to kill pathogens, such as bacteria, when the web comes into contact with them.

However, as concern grows about allergic or toxological reactions to chemicals and about the increasing resistance of bacteria to common antibacterial agents and drug treatments, it has become more desirous to avoid harsh chemicals while still providing a bacteria removing web.

Many pathogens are generally electrostatically charged. For example, most bacteria are negatively charged. As such, pathogens, such as bacteria, are susceptible to electrostatic attraction to oppositely charged molecules. For instance, negatively charged bacteria can be attracted to a positively charged molecule, such as a cation. While this attraction may not kill the attracted bacteria, it can help remove the bacteria from its environment.

Tissue products for capturing and trapping negatively charged bacteria however, are generally limited to the application of metal cation solutions to the surface of a web during converting. For example, US Publication No. 2007/0142262 discloses saturating a web with a solution containing an aluminum cation and US Publication No. 2005/0137540 discloses dipping the wipe substrate in a solution containing an aluminum cation and squeezing off the excess. Such prior art methods generally require additional post manufacture converting, which is costly and reduces overall efficiency.

As such, a need currently exists for a tissue product that effectively captures and retains negatively charged matter, such as bacteria, which may be readily manufactured using existing tissue making machinery and without additional converting or treatment.

SUMMARY

It has now been surprisingly discovered that a bacteriostatic tissue product may be manufactured by applying a bacteriostatic creping additive during the creping step of conventional tissue manufacturing. As such, in general, the present disclosure is directed to a bacteriostatic tissue product comprising a tissue sheet that is subjected to a creping process while the bacteriostatic creping additive is being applied. Of particular advantage, the bacteriostatic creping additive can be applied to the base sheet according to the present disclosure in an amount sufficient so as to increase the surface potential of the sheet, thereby improving the product's bacteriostatic properties.

Accordingly, in one aspect the present disclosure provides a creped tissue product comprising a creped tissue web having a first side and a second side; an additive composition comprising cationic polymer having a charge density of at least about 4 equivalents of nitrogen per kilogram present on at least the first side of the creped tissue web; and wherein the product has a surface charge of at least about 2000 mV.

In other aspects the present disclosure provides a creped tissue web comprising a tissue web having a first side and a second side, the tissue web having been creped from a drum dryer to which a creping additive composition has been applied, the creping additive comprising a bacteriostatic component, a water-soluble adhesive component and a water-soluble modifier component.

In still other aspects the present disclosure provides a tissue sheet having a first side and a second side; and a bacteriostatic composition consisting of a cationic polymer having a charge density of at least about 4 equivalents of nitrogen per kilogram present on at least the first side of the tissue sheet; wherein the product has a surface charge of at least about 2000 mV and a bacteria capture efficiency of at least about 98%.

In yet other aspects the present disclosure provides a process for producing a sheet product comprising A process for producing a sheet product comprising applying a creping additive composition comprising a water-soluble cationic polymer having a charge density of at least about 4 equivalents of nitrogen per kilogram to a moving creping surface; pressing a base sheet against the creping surface after the additive composition has been applied; and removing the base sheet from the creping surface.

Other features and aspects of the present disclosure are discussed in greater detail below.

DETAILED DESCRIPTION

In general, the present disclosure is directed to a tissue product comprising an additive composition onto at least the surface of a fibrous article in order to increase the surface potential of the article, while retaining or improving manufacturing efficiency. The additive composition comprises a bacteriostatic component and more preferably a water-soluble adhesive component and a bacteriostatic component. In some aspects, the additive may also contain additional water-soluble modifier components. Tissue products according to the present disclosure can attract and trap negatively charged matter, such as bacteria, into the tissue web. As such, tissue products can pickup bacteria from a surface and substantially hold the bacteria in the sheet to help prevent spreading bacteria to other surfaces.

In one embodiment, the additive composition may be applied topically to the web during a creping process. For instance, in one embodiment, the additive composition may be sprayed onto the web or onto a heated dryer drum in order to adhere the web to the dryer drum. The web can then be creped from the dryer drum. When the additive composition is applied to the web and then adhered to the dryer drum, the composition may be uniformly applied over the surface area of the web or may be applied according to a particular pattern. An exemplary creping process is disclosed in U.S. Pat. No.

Figure 1:
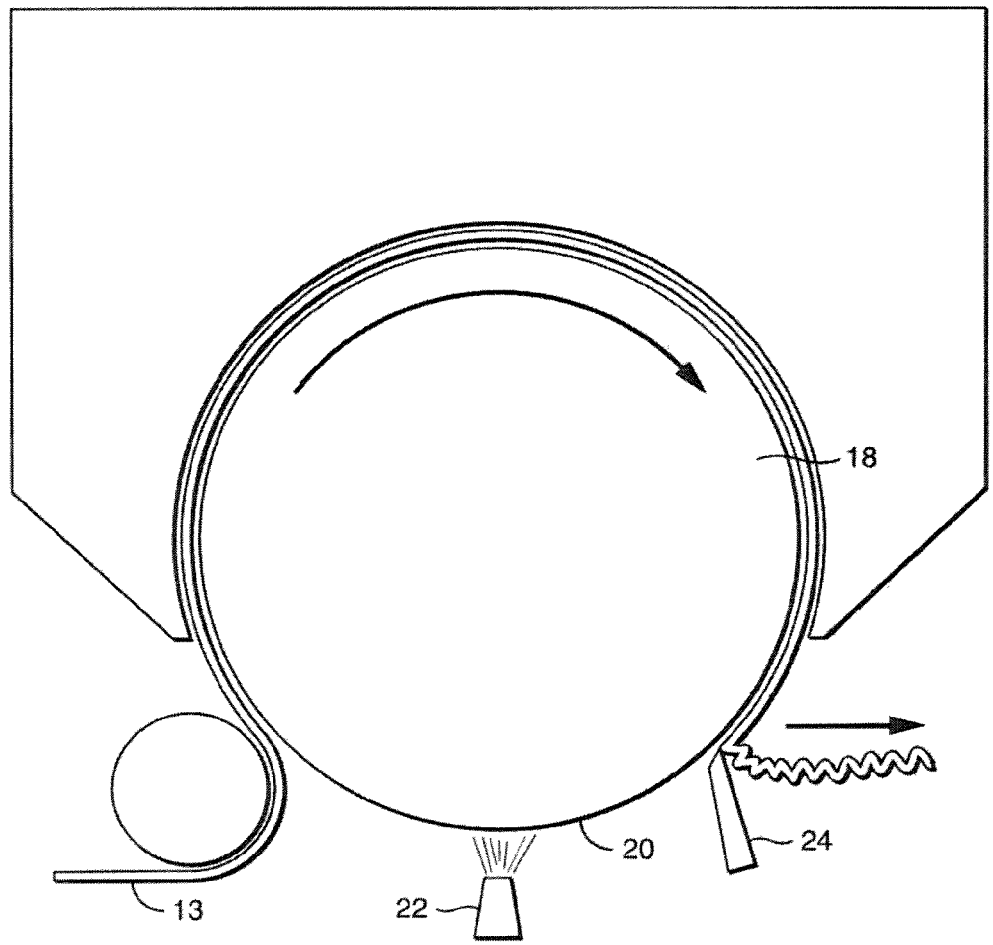
FIG. 1 is a schematic diagram of one aspect of a Yankee dryer used to dry the fibrous web of the present disclosure.

7,820,010, which is incorporated herein by reference in a manner that is consistent herewith. One preferred creping method is illustrated in FIG. 1. In the embodiment illustrated in FIG. 1, the additive composition is applied directly onto the dryer surface 20 (e.g., a Yankee dryer) using a spray boom 22, however other means of application such as printing, foaming and wiping are contemplated. The fibrous web 13 is adhered to the surface of the Yankee dryer when it is pressed into contact with the composition. The fibrous web and the composition are subsequently scraped off of the dryer surface by a creping blade 24.

The additive compositions of the present disclosure function, at the creping blade, like a hot melt adhesive with a high affinity for the metal surface and the cellulosic fiber web along with a low cohesive strength which facilitates failure, at least partially within the creping blend layer on the Yankee dryer, resulting in significant transfer of the creping blend to the cellulosic fiber web. Transfer of significant amounts of the bacteriostatic component in this manner results in a tissue product having a relatively high positive surface charge, which is measured as zeta potential. The term "zeta potential" (also known as "electrokinetic potential") as used herein means a potential gradient that arises across an interface. Thus, once the bacteriostatic component is applied to the sheet surface, the surface maintains a relatively strong positive charge. For example, tissue products according to the present disclosure preferably have a zeta potential of greater than about 2000 mV, more preferably greater than about 4000 mV, and even more preferably, greater than about 6000 mV. Without being bound by any particular theory it is believed that by remaining positively charged the tissue products are well suited for attracting and affixing negatively charged substrates such as bacteria.

Accordingly, in certain embodiments the disclosure provides a bacteriostatic tissue product that is capable of removing and capturing bacteria. In other aspects the bacteriostatic tissue product is also capable of retaining captured bacteria, and preventing the bacteria from being transferred to another surface. In a preferred embodiment the bacteriostatic tissue product has a bacterial removal efficiency of at least about 90%, more preferably at least about 95% and still more preferably at least about 98%. In other embodiments the bacteriostatic tissue product has a bacterial capture efficiency of at least about 95%, more preferably at least about 98% and still more preferably at least about 99%. In still other embodiments the bacteriostatic tissue product has a bacterial transfer efficiency of less than about 2%, more preferably less than about 1% and still more preferably less than about 0.5%, such as from about 0.05% to about 0.5%.

To achieve the desired positive surface charge tissue products are treated with an additive composition comprising a bacteriostatic component. Preferably the bacteriostatic component is a cationic polymer having a relatively low-molecular-weight, preferably having molecular weights of at least about 50,000 and no more than about 500,000 and more preferably not more than about 300,000. Preferably the cationic polymer has a relatively high charge density, for example, a charge density of at least about 4, and more preferably at least about 8, and still more preferably at least about 12, equivalents of cationic nitrogen per kilogram of polymer.

In a particularly preferred embodiment the bacteriostatic component is a water-soluble cationic polymer having a molecular weight of from about 100,000 to 200,000. As used herein, the term "water-soluble" refers to materials which dissolve completely in water at 37° C. to give a true solution as opposed to materials which form a latex or suspension of undissolved particles. Preferably the water-soluble cationic polymer has a relatively high charge density, for example a charge density of at least about 4 and more preferably at least about 8 and still more preferably at least about 12, equivalents of cationic nitrogen per kilogram of polymer. Suitable water-soluble cationic polymers include quaternized copolymers of vinylpyrrolidone (VP), methacrylamide (MAM), vinylimidazole (VI) and quaternized vinylimidazole (QVI). For example, polyquaternium-68, polyquaternium-44, polyquaternium-46, polyquaternium-16 and polyquaternium-11, all of which are available from BASF Aktiengesellschaft, Ludwigshafen, Germany under the trade name Luviquat®. Particularly preferred water-soluble cationic polymers include polymers comprising the monomer diallyl dimethyl ammonium chloride (DADMAC), for example, polyquaternium-6, polyquaternium-7 and polyquaternium-39, available from Nalco Co., Naperville, Ill. An exemplary water-soluble cationic polymer is polyquaternium-6, poly (diallyl dimethyl ammonium chloride) (polyDADMAC), available from Nalco Co., Naperville, Ill. under the trade name Merquat® 100.

The bacteriostatic component can be present in the additive composition in any operative amount and will vary based on the chemical component selected, as well as on the end properties that are desired. For example, in the exemplary case of Merquat® 100, the bacteriostatic component can be present in the additive composition in an amount of about 10-90 wt %, such as 20-80 wt % or 30-70 wt % based on the total weight of the additive composition, to provide improved benefits.

In a preferred embodiment the additive composition further comprises at least one water-soluble adhesive component capable of adhering the web to the surface of a dryer. Preferably the water-soluble adhesive component is non-cross-linking. The advantage of using essentially non-cross-linking polymers is that the rheology of the polymer system in solution is substantially retained when a dried film is formed of the soluble components even when the film is heated such as when the polymer is sprayed onto the surface of a Yankee dryer. The water-soluble adhesive component contained within the additive composition may vary depending upon the particular application and the desired result. In a preferred embodiment, the adhesive component is the polymerization product of a cationic acrylate or methacrylate and one or more alkyl acrylates or methacrylates having the generic structure:

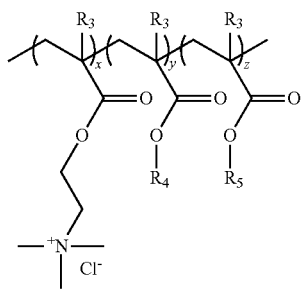

wherein x=1 to about 15 mol %; y=about 60 to about 99 mol %; and z=0 to about 30 mol %; $R_4$ is selected from methyl and ethyl; $R_5$ is selected from hydrogen, methyl, ethyl, butyl, ethylhexyl, decyl, dodecyl, hydroxyethyl, hydroxypropyl, polyoxyethylene, and polyoxypropylene.

In an especially preferred embodiment of the present disclosure, the water-soluble adhesive component has the structure:

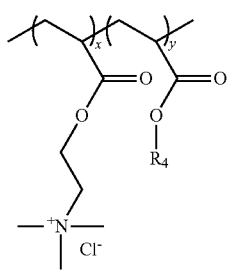

wherein x=1 to about 15 mol %; y=about 85 to about 99 mol % and $R_4$ is $C_1$-$C_4$ alkyl. In a most desirable embodiment, when $R_4$ is methyl, x=3 to about 6 mol %; y=about 94 to about 97 mol %. A particularly preferred water-soluble adhesive component is a cationic polyacrylate that is the polymerization product of 96 mol % methyl acrylate and 4 mol % [2-(acryloyloxy)ethyl]trimethyl ammonium chloride, also referred to herein as L7170, which is disclosed in U.S. Pat. No. 7,157,389, which is incorporated herein in a manner consistent herewith.

The water-soluble adhesive components of the present disclosure may have an average molecular weight that varies depending on the ultimate use of the polymer. The water-soluble adhesive components of the present disclosure have a weight average molecular weight ranging from about 5,000 to about 500,000 grams per mol. More specifically, the water-soluble adhesive components of the present disclosure have a weight average molecular weight ranging from about 8,000 to about 500,000 grams per mol.

The water-soluble adhesive component can be present in the additive composition in any operative amount and will vary based on the chemical component selected, as well as on the end properties that are desired. For example, in the exemplary case of L7170, the water-soluble adhesive component can be present in the additive composition in an amount of about 10-90 wt %, such as 20-80 wt % or 30-70 wt % based on the total weight of the additive composition, to provide improved benefits.

In some aspects, the water-soluble adhesive component is dissolved into a 1 wt % aqueous solution, and diluted further as required to provide the desired dosage in mg/m² of tissue surface. The dosage is estimated based on the volume of adhesive solution multiplied by the adhesive concentration and divided by the square meters of tissue treated per unit time. For example, in the exemplary case of L7170 the water-soluble adhesive component can be present in the additive composition in an amount of about 1-70 wt %, or at least about 1 wt %, such as at least about 5 wt %, or least about 10 wt %, or up to about 30 wt %, such as up to about 50 wt % or up to about 75 wt % or more, based on the total weight of the additive composition, to provide improved benefits. Any of these chemistries, once diluted in water, are disposed onto a Yankee dryer surface with a spray boom 22 to ultimately transfer to the web surface.

In addition to a water-soluble adhesive component, the additive composition may also comprise a water-soluble modifier component. The water-soluble modifier component is used, among other things, to adjust adhesion of the web to a paper drying surface. The water-soluble modifier component can also improve paper machine cleanliness (e.g., the paper machine dryer surface and paper machine felts or fabrics). In some aspects, the water-soluble modifier component is a first water-soluble modifier component. In one particular aspect, the water-soluble modifier component is Carbowax PEG 8000 (Dow Chemical, Midland, Mich.). In another aspect, the water soluble modifier component is Jeffamine ED2003 (Huntsman Petrochemical Corp., The Woodlands, Tex.). The water-soluble modifier component can be present in the additive composition in any operative amount and will vary based on the chemical component selected, as well as on the end properties that are desired. For example, in the exemplary case of Carbowax PEG 8000, the water-soluble modifier component can be present in the additive composition in an amount of about 1-60 wt %, or at least about 1 wt %, such as at least about 5 wt %, or least about 10 wt %, or up to about 30 wt %, such as up to about 50 wt % or more, based on the total weight of the additive composition, to provide improved benefits.

In some aspects, the additive composition can be diluted prior to application. The pH of the aqueous solution is generally less than about 12, such as from about 5 to about 9, and preferably about 6 to about 8. In this aspect, the additive composition can be diluted to between 0.20 wt % to 10 wt %, desirably to between 4 to 7 wt %.

In one embodiment, the additive composition may be applied topically to the web during a creping process. For instance, the additive composition may be sprayed onto a heated dryer drum in order to adhere the web to the dryer drum. The web can then be creped from the dryer drum.

In general, any suitable fibrous web may be treated in accordance with the present disclosure. For example, in one aspect, the base sheet can be a tissue product, such as a bath tissue, a facial tissue, a paper towel, a napkin, dry and moist wipes, and the like. Fibrous products can be made from any suitable types of fiber. Fibrous products made according to the present disclosure may include single-ply fibrous products or multiple-ply fibrous products. For instance, in some aspects, the product may include two plies, three plies, or more.

Fibers suitable for making fibrous webs comprise any natural or synthetic fibers including, but not limited to nonwoody fibers, such as cotton, abaca, kenaf, sabai grass, flax, esparto grass, straw, jute hemp, bagasse, milkweed floss fibers, and pineapple leaf fibers; and woody or pulp fibers such as those obtained from deciduous and coniferous trees, including softwood fibers, such as northern and southern softwood kraft fibers; hardwood fibers, such as eucalyptus, maple, birch, and aspen. Pulp fibers can be prepared in high-yield or low-yield forms and can be pulped in any known method, including kraft, sulfite, high-yield pulping methods and other known pulping methods. Fibers prepared from organosolv pulping methods can also be used, including the fibers and methods disclosed in U.S. Pat. Nos. 4,793,898, 4,594,130, 3,585,104. Useful fibers can also be produced by anthraquinone pulping, exemplified by U.S. Pat. No. 5,595,628.

The fibrous webs of the present disclosure can also include synthetic fibers. For instance, the fibrous webs can include up to about 10%, such as up to about 30% or up to about 50% or up to about 70% or more by dry weight, to provide improved benefits. Suitable synthetic fibers include rayon, polyolefin fibers, polyester fibers, bicomponent sheath-core fibers, multi-component binder fibers, and the like. Synthetic cellulose fiber types include rayon in all its varieties and other fibers derived from viscose or chemically-modified cellulose.

Chemically treated natural cellulosic fibers can be used, for example, mercerized pulps, chemically stiffened or crosslinked fibers, or sulfonated fibers. For good mechanical properties in using web forming fibers, it can be desirable that the fibers be relatively undamaged and largely unrefined or only lightly refined. While recycled fibers can be used, virgin fibers are generally useful for their mechanical properties and lack of contaminants. Mercerized fibers, regenerated cellulosic fibers, cellulose produced by microbes, rayon, and other cellulosic material or cellulosic derivatives can be used. Suitable web forming fibers can also include recycled fibers, virgin fibers, or mixes thereof.

In general, any process capable of forming a web can also be utilized in the present disclosure. For example, a web forming process of the present disclosure can utilize creping, wet creping, double creping, recreping, double recreping, embossing, wet pressing, air pressing, through-air drying, hydroentangling, creped through-air drying, co-forming, air laying, as well as other processes known in the art. For hydroentangled material, the percentage of pulp is about 70-85%.

Also suitable for articles of the present disclosure are fibrous sheets that are pattern densified or imprinted, such as the fibrous sheets disclosed in any of the following U.S. Pat. Nos. 4,514,345, 4,528,239, 5,098,522, 5,260,171, and 5,624,790, the disclosures of which are incorporated herein by reference to the extent that they are non-contradictory herewith. Such imprinted fibrous sheets may have a network of densified regions that have been imprinted against a drum dryer by an imprinting fabric, and regions that are relatively less densified (e.g., "domes" in the fibrous sheet) corresponding to deflection conduits in the imprinting fabric, wherein the fibrous sheet superposed over the deflection conduits was deflected by an air pressure differential across the deflection conduit to form a lower-density pillow-like region or dome in the fibrous sheet.

The fibrous web can also be formed without a substantial amount of inner fiber-to-fiber bond strength. In this regard, the fiber furnish used to form the base web can be treated with a chemical debonding agent. The debonding agent can be added to the fiber slurry during the pulping process or can be added directly to the headbox. Suitable debonding agents that may be used in the present disclosure include cationic debonding agents such as fatty dialkyl quaternary amine salts, mono fatty alkyl tertiary amine salts, primary amine salts, imidazoline quaternary salts, silicone, quaternary salt and unsaturated fatty alkyl amine salts. Other suitable debonding agents are disclosed in U.S. Pat. No. 5,529,665, which is incorporated herein by reference in a manner consistent herewith.

Optional chemical additives may also be added to the aqueous web forming furnish or to the formed embryonic web to impart additional benefits to the product and process and are not antagonistic to the intended benefits of the invention. The following chemicals are included as examples and are not intended to limit the scope of the invention.

The types of chemicals that may be added to the paper web include absorbency aids usually in the form of cationic, or non-ionic surfactants, humectants and plasticizers such as low molecular weight polyethylene glycols and polyhydroxy compounds such as glycerin and propylene glycol. Materials that supply skin health benefits such as mineral oil, aloe extract, vitamin-E, silicone, lotions in general, and the like, may also be incorporated into the finished products. Such chemicals may be added at any point in the web forming process.

In general, the products of the present disclosure can be used in conjunction with any known materials and chemicals that are not antagonistic to its intended use. Examples of such materials include but are not limited to odor control agents, such as odor absorbents, activated carbon fibers and particles, baby powder, baking soda, chelating agents, zeolites, perfumes or other odor-masking agents, cyclodextrin compounds, oxidizers, and the like. Superabsorbent particles, synthetic fibers, or films may also be employed. Additional options include cationic dyes, optical brighteners, humectants, emollients, and the like.

Fibrous webs that may be treated in accordance with the present disclosure may include a single homogenous layer of fibers or may include a stratified or layered construction. For instance, the fibrous web ply may include two or three layers of fibers. Each layer may have a different fiber composition. For example, referring to FIG. 3, one aspect of a device for forming a multi-layered stratified pulp furnish is illustrated. As shown, a three-layered headbox 10 generally includes an upper head box wall 12 and a lower head box wall 14. Headbox 10 further includes a first divider 16 and a second divider 19, which separate three fiber stock layers.

Each of the fiber layers comprises a dilute aqueous suspension of papermaking fibers. The particular fibers contained in each layer generally depend upon the product being formed and the desired results. For instance, the fiber composition of each layer may vary depending upon whether a bath tissue product, facial tissue product or paper towel is being produced. In one aspect, for instance, middle layer 21 contains southern softwood kraft fibers either alone or in combination with other fibers such as high yield fibers. Outer layers 23 and 25, on the other hand, contain softwood fibers, such as northern softwood kraft.

In an alternative aspect, the middle layer may contain softwood fibers for strength, while the outer layers may comprise hardwood fibers, such as eucalyptus fibers, for a perceived softness.

Figure 3:
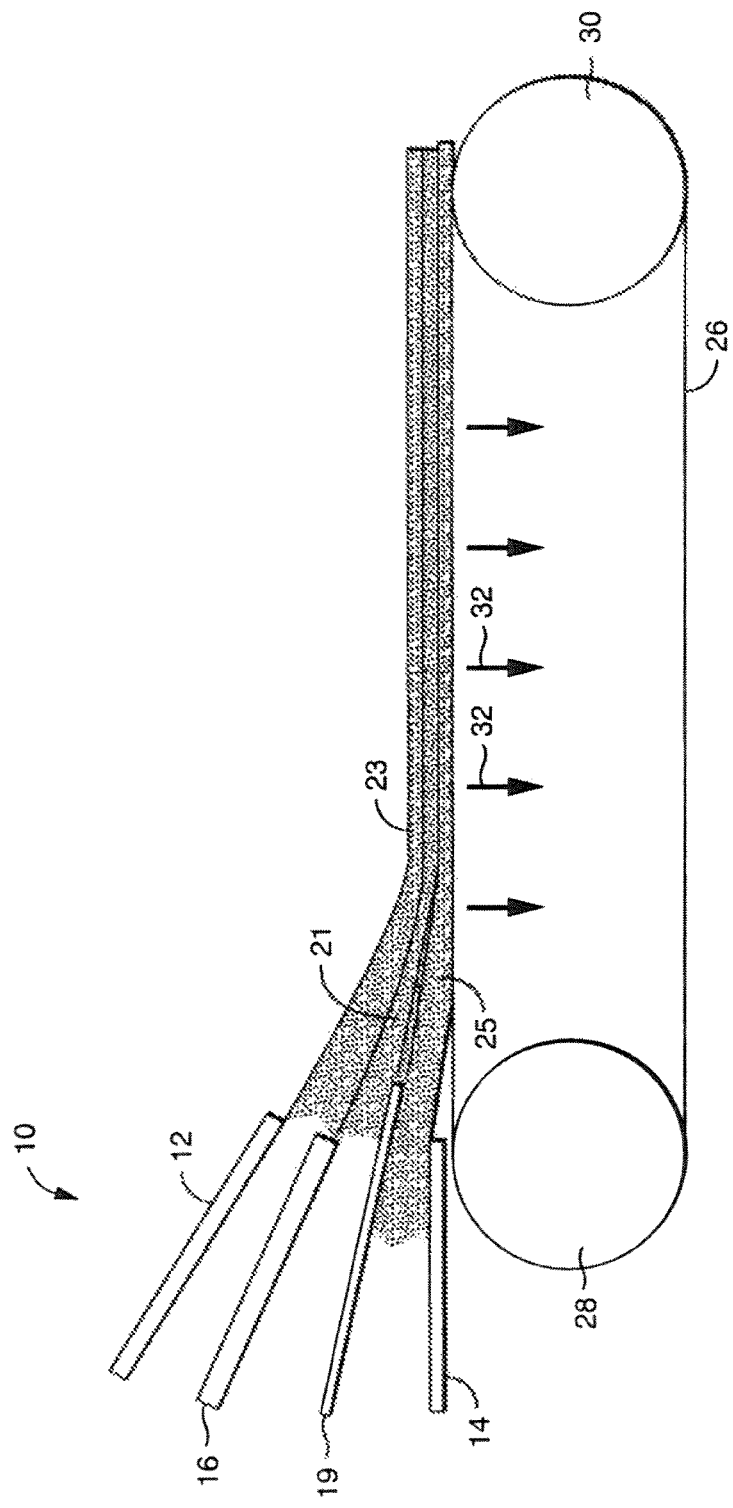
FIG. 3 is a schematic diagram of one portion of a fibrous web forming machine, illustrating one aspect of the formation of a stratified fibrous web having multiple layers.

In general, any process capable of forming a base sheet may be utilized in the present disclosure. For example, as illustrated in FIG. 3, an endless traveling forming fabric 26, suitably supported and driven by rolls 28 and 30, receives the layered papermaking stock issuing from headbox 10. Once retained on fabric 26, the layered fiber suspension passes water through the fabric as shown by the arrows 32. Water removal is achieved by combinations of gravity, centrifugal force and vacuum suction depending on the forming configuration. Forming multi-layered paper webs is also described and disclosed in U.S. Pat. No. 5,129,988, which is incorporated herein by reference in a manner that is consistent herewith.

The basis weight of fibrous webs made in accordance with the present disclosure can vary depending upon the final product. For example, the process may be used to produce bath tissues, facial tissues, paper towels, and the like. In general, the basis weight of such fibrous products may vary from about 5 gsm to about 110 gsm, such as from about 10 gsm to about 90 gsm. For bath tissue and facial tissues, for instance, the basis weight may range from about 10 gsm to about 40 gsm. For paper towels, on the other hand, the basis weight may range from about 25 gsm to about 80 gsm or more.

Fibrous products made according to the above processes can have relatively good bulk characteristics. For instance, the fibrous web bulk may also vary from about 1-20 cc/g, such as from about 3-15 cc/g or from about 5-12 cc/g.

In multiple-ply products, the basis weight of each fibrous web present in the product can also vary. In general, the total basis weight of a multiple ply product will generally be the same as indicated above, such as from about 20 gsm to about 200 gsm. Thus, the basis weight of each ply can be from about 10 gsm to about 60 gsm, such as from about 20 gsm to about 40 gsm.

Figure 2:
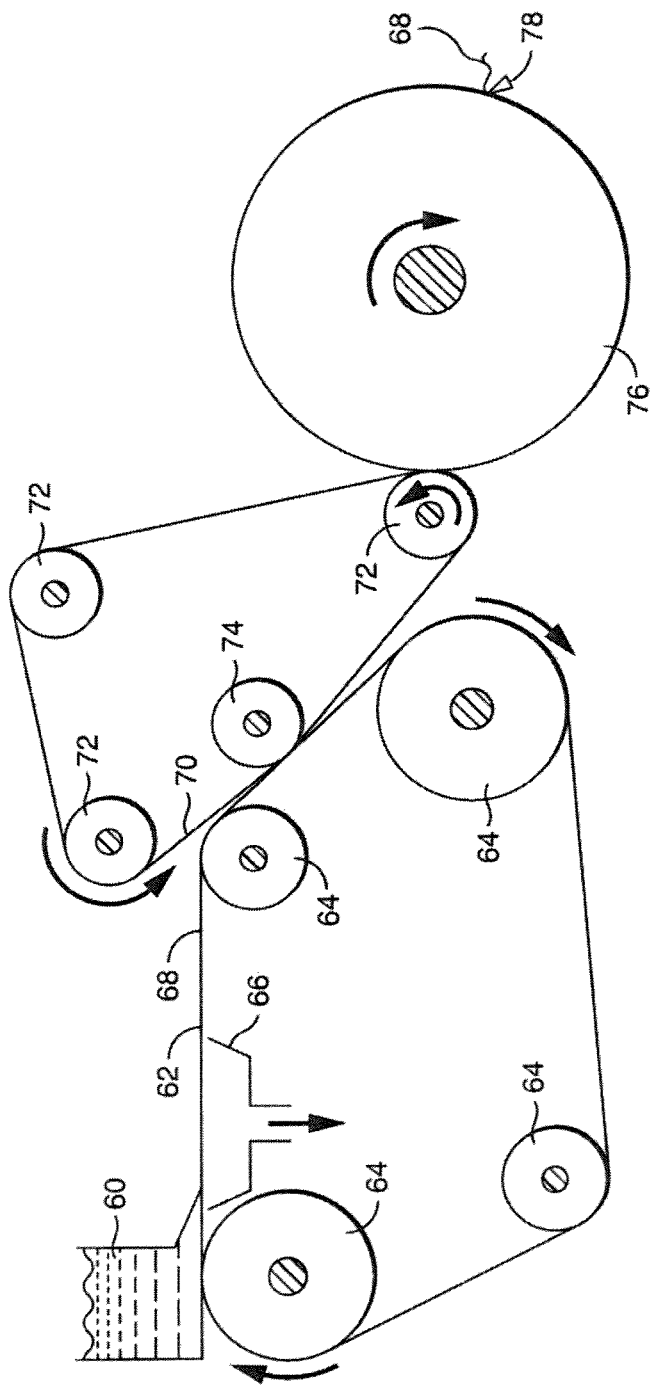
FIG. 2 is a is a schematic diagram of one aspect of a process for forming wet creped fibrous webs for use in the present disclosure.

Now with reference to FIG. 2, a headbox 60 emits an aqueous suspension of fibers onto a forming fabric 62 which is supported and driven by a plurality of guide rolls 64. A vacuum box 66 is disposed beneath forming fabric 62 and is adapted to remove water from the fiber furnish to assist in forming a web. From forming fabric 62, a formed web 68 is transferred to a second fabric 70, which may be either a wire or a felt. Fabric 70 is supported for movement around a continuous path by a plurality of guide rolls 72. Also included is a pick up roll 74 designed to facilitate transfer of web 68 from fabric 62 to fabric 70.

Preferably the formed web is dried by transfer to the surface of a rotatable heated dryer drum, such as a Yankee dryer. In accordance with the present disclosure, the additive composition of the present disclosure may be applied topically to the tissue web while the web is traveling on the fabric or may be applied to the surface of the dryer drum for transfer onto one side of the tissue web. In this manner, the additive composition is used to adhere the tissue web to the dryer drum. In this embodiment, as web is carried through a portion of the rotational path of the dryer surface, heat is imparted to the web causing most of the moisture contained within the web to be evaporated. Web is then removed from dryer drum by a creping blade. Creping web as it is formed further reduces internal bonding within the web and increases softness. Applying the additive composition to the web during creping, on the other hand, may increase the strength of the web.

In another embodiment the formed web is transferred to the surface of the rotatable heated dryer drum, which may be a Yankee dryer. The press roll may, in one embodiment, comprise a suction breast roll. In order to adhere the web to the surface of the dryer drum, a creping adhesive may be applied to the surface of the dryer drum by a spraying device. The spraying device may emit an additive composition made in accordance with the present disclosure or may emit a conventional creping adhesive. The web is adhered to the surface of the dryer drum and then creped from the drum using the creping blade. If desired, the dryer drum may be associated with a hood. The hood may be used to force air against or through the web.

In other embodiments, once creped from the dryer drum, the web may be adhered to a second dryer drum. The second dryer drum may comprise, for instance, a heated drum surrounded by a hood. The drum may be heated from about 25° C. to about 200° C., such as from about 100° C. to about 150° C.

In order to adhere the web to the second dryer drum, a second spray device may emit an adhesive onto the surface of the dryer drum. In accordance with the present disclosure, for instance, the second spray device may emit an additive composition as described above. The additive composition not only assists in adhering the tissue web to the dryer drum, but also is transferred to the surface of the web as the web is creped from the dryer drum by the creping blade.

Once creped from the second dryer drum, the web may, optionally, be fed around a cooling reel drum and cooled prior to being wound on a reel.

In addition to applying the additive composition during formation of the fibrous web, the additive composition may also be used in post-forming processes. For example, in one aspect, the additive composition may be used during a print-creping process. Specifically, once topically applied to a fibrous web, the additive composition has been found well-suited to adhering the fibrous web to a creping surface, such as in a print-creping operation.

For example, once a fibrous web is formed and dried, in one aspect, the additive composition may be applied to at least one side of the web and the at least one side of the web may then be creped. In general, the additive composition may be applied to only one side of the web and only one side of the web may be creped, the additive composition may be applied to both sides of the web and only one side of the web is creped, or the additive composition may be applied to each side of the web and each side of the web may be creped.

In one embodiment the additive composition may be added to one side of the web by creping, using either an in-line or off-line process. A tissue web made according to the process illustrated in FIG. 2 or FIG. 3 or according to a similar process is passed through a first additive composition application station that includes a nip formed by a smooth rubber press roll and a patterned rotogravure roll. The rotogravure roll is in communication with a reservoir containing a first additive composition. The rotogravure roll applies the additive composition to one side of web in a preselected pattern. The web is then contacted with a heated roll, which can be heated to a temperature, for instance, up to about 200° C., and more preferably from about 100° C. to about 150° C. In general, the web can be heated to a temperature sufficient to dry the web and evaporate any water. It should be understood, that the besides the heated roll, any suitable heating device can be used to dry the web. For example, in an alternative embodiment, the web can be placed in communication with an infra-red heater in order to dry the web. Besides using a heated roll or an infra-red heater, other heating devices can include, for instance, any suitable convective oven or microwave oven.

From the heated roll, the web can be advanced by pull rolls to a second additive composition application station, which includes a transfer roll in contact with a rotogravure roll, which is in communication with a reservoir containing a second additive composition. The second additive composition may be applied to the opposite side of web in a preselected pattern. The first and second additive compositions may contain the same ingredients or may contain different ingredients. Alternatively, the additive compositions may contain the same ingredients in different amounts as desired. Once the second additive composition is applied the web is adhered to a creping roll by a press roll and carried on the surface of the creping drum for a distance and then removed therefrom by the action of a creping blade. The creping blade performs a controlled pattern creping operation on the second side of the tissue web. Although the additive composition is being applied to each side of the tissue web, only one side of the web undergoes a creping process. It should be understood, however, that in other embodiments both sides of the web may be creped.

Once creped the tissue web may be pulled through a drying station. The drying station can include any form of a heating unit, such as an oven energized by infra-red heat, microwave energy, hot air or the like. A drying station may be necessary in some applications to dry the web and/or cure the additive composition. Depending upon the additive composition selected, however, in other applications a drying station may not be needed.

According to the present disclosure, the additive composition is applied to the paper web so as to cover from about 15% to about 100% of the surface area of the web. More particularly, in most applications, the additive composition will cover from about 20% to about 60% of the surface area of each side of the web. The total amount of additive composition applied to each side of the web can be in the range of from about 0.1% to about 10% by weight, based upon the total weight of the web, such as from about 0.3% to about 5% by weight, such as from about 0.5% to about 3% by weight. To achieve the desired additive application levels the add on rate of additive composition to the dryer, measured as mass (i.e., mg) per unit area of dryer surface (i.e., $m^2$), may range from about 50 mg/m² to about 200 mg/m², and still more preferably from about 100 to about 150 mg/m².

In one aspect, fibrous webs made according to the present disclosure can be incorporated into multiple-ply products. For instance, in one aspect, a fibrous web made according to the present disclosure can be attached to one or more other fibrous webs for forming a wiping product having desired characteristics. The other webs laminated to the fibrous web of the present disclosure can be, for instance, a wet-creped web, a calendered web, an embossed web, a through-air dried web, a creped through-air dried web, an uncreped through-air dried web, an airlaid web, and the like.

In one aspect, when incorporating a fibrous web made according to the present disclosure into a multiple-ply product, it may be desirable to only apply the additive composition to one side of the fibrous web and to thereafter crepe the treated side of the web. The creped side of the web is then used to form an exterior surface of a multiple-ply product. The untreated and uncreped side of the web, on the other hand, is attached by any suitable means to one or more plies.

Tissue sheets made according to the present disclosure may possess a desirable quality whereby the tissue sheet is capable of removing negatively charged matter, particularly bacteria, through wiping. Preferably the tissue sheets remove at least about 97% of the bacteria, more preferably 98% and still more preferably at least about 99%. The efficacy of bacteria removal from a surface by wiping with a tissue product is referred to herein as "bacteria removal efficiency." The method used to determine the amount of bacteria removed from a skin simulant by wiping with a tissue product is described in the Test Method section.

Tissue sheets made according to the present disclosure may also possess a desirable quality whereby the tissue sheet is capable of retaining negatively charged matter, particularly bacteria, after wiping the negatively charged matter from a surface. Preferably the tissue sheets retain at least about 97% of the bacteria, more preferably 98% and still more preferably at least about 99%. The ability of the tissue product to retain captured bacteria is referred to herein as "bacteria capture efficiency." The method used to determine the amount of bacteria retained on the tissue product after wiping is described in the Test Method section.

Tissue sheets made according to the present disclosure may also possess a desirable quality whereby negatively charged matter, particularly bacteria, captured by the tissue product are retained on the sheet and have low levels of transferring to other surfaces contacted by the sheet. Preferably incidents of transfer are less than about 2%, more preferably less than about 1% and still more preferably less than about 0.5%. The transfer of bacteria captured and retained on a tissue product to another surface is referred to herein as "bacteria transfer efficiency." The method used to determine the amount of bacteria transferred from a tissue sheet that has been used to capture and retain bacteria to another surface is described in the Test Method section.

Test Methods

Streaming Zeta Potential Analysis

When a solid with an electrical charge on its surface is placed in water, an "electrical double layer" is formed against the charged surface that is facing the water. This formation is driven by balance of charge. There are two parts of the double layer. One is an immobile layer (known in the field as the "stern layer"), which is predominantly made up of opposite (relative to the charged surface) charged species. The second layer is a mobile layer (known in the field as the "diffuse layer"), which is predominantly made up of similar (relative to the charged surface) charged species. In absolutely pure water ($H_2O$), these species are $OH^-$ and $H^+$. When there exists flow or directional motion in the water, the diffuse layer can be sheared off (i.e., the charged species in this layer moves in the motion of the flow); and the degree/rate of shearing is dependent on the surface charge of the solid in contact with the water.

A technique known as streaming Zeta potential is used to measure the surface charge. This technique measures how fast the charged species that is sheared via streaming water containing $K^+$ and $Cl^-$ ions against the charged surface to be measured. This is done by measuring the change in conductance at two detecting electrodes; the change in conductance is dependent on the velocity by which $K^+$ species and $Cl^-$ species come into contact with the electrodes. The surface charge, Zeta potential, is calculated using the formula published by D. Fairhurst and V. Ribitsch (Particle Size Distribution II, Assessment and Characterization, Chapter 22, ACS Symposium Series 472, Edited by Provider, Theodore, ISBN 0841221170).

During the sample preparation, treated and untreated wipe substrates were cut to two identical pieces (120 mm×50 mm) and then placed into the sample cell with Teflon™ between them. After the sample cell was mounted onto the instrument, all the air bubbles were removed by purging. Then KCl solution (1 mM, pH=5.9, Temp=22° C.) was forced through the two layers of the media and Ag/AgCl electrodes were used to measure the streaming potential. All samples were tested under similar pH, solution conductivity and using the same number of spacers. The measurement is carried out on an Electro Kinetic Analyzer (EKA) (Anton Paar® GmbH, Graz, Austria) equipped with an IKS 100 Control and Evaluation Software for EKA. Detailed procedures are described in the manual Anton Paar EKA Electro Kinetic Analyzer Part II: Operating the EKA Instruction Handbook (Doc. No. A481B08-B).

Bacteria Removal, Capture and Transfer

To determine how efficient the substrate and treatment were in holding bacteria cleaned from the surface, the following test procedure was carried out.

An inoculating broth was prepared as follows: *S. aureus* ATCC 27660 was streaked onto a tryptic soy agar (TSA) plate (Hanil Komed Co., Ltd, Korea) and incubated at 35° C. After 24 hours of incubation three to five individual colonies were picked with a sterile inoculating loop and used to inoculate 10 mL of growth medium. The tube of inoculated growth medium was incubated at 35° C. in atmospheric air. After 24 hours of incubation, the culture was removed from the incubator and mixed well on an S/P brand vortex mixer. A second tube containing 10 mL of the growth medium was inoculated with 0.5 mL of the above-described 24 hour old culture and incubated at 35° C. in atmospheric air. After 24 hours of incubation the culture was removed from the incubator and mixed well on an S/P brand vortex mixer. The optical density of the culture fluid was determined in a microplate reader (Bio-Tek Instruments, Model EL309, Winooski, Vt.). The amount of inoculum necessary to give $5 \times 10^6$ CFU/mL in 10 mL of growth medium was determined using a standard curve. For testing 100 μL aliquots of the diluted inoculums were prepared. To each aliquot bovine serum albumin (BSA) was added to achieve a final concentration of $5 \times 10^6$ CFU/mL.

For testing the diluted inoculum was applied to VITRO-SKIN™ N-19-5X (IMS Inc., Portland, Me.) that had been cut into 5×5 cm pieces. The VITRO-SKIN™ pieces were hydrated overnight at saturated condition, 23° C. After hydrating each 5×5 cm piece of VITRO-SKIN™ 100 μL of the S. aureus inoculums ($5 \times 10^6$ CFU/mL) was added to the surface of the VITRO-SKIN™ by pipette. The inoculated VITRO-SKIN™ pieces were then transferred to a UniSlide® Assemblies A 2509A-S2.5 (Velmex. Inc., Bloomfield, N.Y.) wiping machine and wiped 5 times at a pressure of approximately 1.65 psi with either a treated or untreated tissue product.

To determine how effectively each tissue product removed bacteria from the VITRO-SKIN™, i.e., bacterial removal efficiency, the amount of bacteria retained on the VITRO-SKIN™ after wiping was determined. The wiped VITRO-SKIN™ was transferred to a 50 mL tube and 30 mL of sterile letheen broth was added. The tubes were sonicated (5 cycles of 1 minute on, 1 minute off) in a water bath to dislodge any bacteria that is not bound tightly to the VITRO-SKIN™. One hundred microliters of the letheen broth from the tubes containing the VITRO-SKIN™ were plated in duplicate onto TSA (Tryptic Soy Agar) plates. The plates were incubated at 37° C. and the number of colony forming units per mL after incubation was determined by standard plate count procedures. Bacterial removal efficiency was then calculated as follows:

$$\text{Bacteria Removal Efficiency} = \frac{5 \times 10^6 CFU/mL - ([S.aueus] \text{on SKIN after wiping})}{5 \times 10^6 CFU/mL} \times 100$$

To determine how effectively each tissue product retained bacteria, i.e., bacterial capture efficiency, after wiping the VITRO-SKIN™ pieces each tissue product was transferred to a 15 mL tube and 10 mL of sterile letheen broth was added. The tubes were sonicated (5 cycles of 1 minute on, 1 minute off) in a water bath to dislodge any bacteria that is not bound tightly to the tissue product. One hundred microliters of the letheen broth from the tubes containing the material were plated in duplicate onto TSA (Tryptic Soy Agar) plates. The plates were incubated at 37° C. and the number of colony forming units per mL after incubation was determined by standard plate count procedures. Bacterial capture efficiency was then calculated as follows:

$$\text{Bacteria Capture Efficiency} = \frac{([S.aueus] \text{removed from SKIN}) - ([S.aueus] \text{in solution after sonication})}{([S.aueus] \text{removed from SKIN})} \times 100$$

To further determine how effectively each tissue product retained bacteria a test was performed to determine the amount of bacteria transferred from a contaminated tissue product to uncontaminated skin, i.e., bacterial transfer efficiency. After wiping the VITRO-SKIN™ pieces as described above, the contaminated tissue product was used to wipe a second, uninoculated 5×5 cm piece of VITRO-SKIN™. The second piece of VITRO-SKIN™ was transferred to a 50 mL tube and 30 mL of sterile letheen broth was added. The tubes were sonicated (5 cycles of 1 minute on, 1 minute off) in a water bath to dislodge any bacteria that is not bound tightly to the VITRO-SKIN™. One hundred microliters of the letheen broth from the tubes containing the VITRO-SKIN™ were plated in duplicate onto LB agar plates. The plates were incubated at 37° C. and the number of colony forming units per mL after incubation was determined by standard plate count procedures. Bacterial transfer efficiency was then calculated as follows:

$$\text{Bacteria Transfer Efficiency} = \frac{[S.aueus] \text{on second SKIN}}{([S.aueus] \text{removed from first SKIN})} \times 100$$

EXAMPLES

In this example, fibrous webs were made generally according to the process illustrated in FIG. 2. In order to adhere the fibrous web to a creping surface, which in this example comprised a Yankee dryer, additive compositions made according to the present disclosure were sprayed onto the dryer prior to contacting the dryer with the web. The samples were then subjected to various standardized tests.

For purposes of comparison, samples were also produced using a conventional creping chemistry treatment as a control. Samples were also produced using an additive composition having a blend composed of 91.7% Polyvinyl alcohol (Wacker Chemie AG, Calvert City, Ky.), 7.6% Kymene and 0.7% Rezosol 1095 (both available from Ashland, Inc., Covington, Ky.). This blend is diluted with water to provide an application rate of 15 mg/m² of tissue surface. In this example, 2-ply facial tissue products were produced and tested according to the same tests described in the Test Methods section. The following tissue manufacturing process was used to produce the samples.

Initially, northern softwood kraft (NSWK) pulp was dispersed in a pulper for 30 minutes at 4% consistency at about 100° F. The NSWK pulp was then transferred to a dump chest and subsequently diluted to approximately 3% consistency. The NSWK pulp was refined at 4.5-5.5 hp-days/metric ton. The softwood fibers were used as the inner strength layer in a 3-layer tissue structure. The NSWK layer contributed approximately 34-38% of the final sheet weight.

Two kilograms KYMENE™ 6500, 2-5 kilograms Hercobond™ 1366 (Ashland, Inc., Covington, Ky.) per metric ton of wood fiber was added to the NSWK pulp prior to the headbox.

Aracruz ECF, a eucalyptus hardwood Kraft (EHWK) pulp (Aracruz, Rio de Janeiro, RJ, Brazil) was dispersed in a pulper for 30 minutes at about 4% consistency at about 100° F. The EHWK pulp was then transferred to a dump chest and subsequently diluted to about 3% consistency. The EHWK pulp fibers were used in the two outer layers of the 3-layered tissue structure. The EHWK layers contributed approximately 62-66% of the final sheet weight.

The pulp fibers from the machine chests were pumped to the headbox at a consistency of about 0.1%. Pulp fibers from each machine chest were sent through separate manifolds in the headbox to create a 3-layered tissue structure. The fibers were deposited onto a felt in a fourdrenier type of former.

The wet sheet, about 10-20% consistency, was adhered to a Yankee dryer, traveling at about 50 to about 60 fpm (15 mpm-18 mpm) through a nip via a pressure roll.

The consistency of the wet sheet after the pressure roll nip (post-pressure roll consistency or PPRC) was approximately 40%. The wet sheet is adhered to the Yankee dryer due to the additive composition that is applied to the dryer surface. Spray booms situated underneath the Yankee dryer sprayed the creping/additive composition, described in the present disclosure, onto the dryer surface at addition levels of about 150 mg/m².

The creping additive comprising L7170, PEG 8000, and Merquat® 100 was prepared by dissolution of the solid polymers into water followed by stirring until the solution was homogeneous. L7170 at 24% solids and PEG 8000 at 20% solids and Merquat® 100 at 41% solids were added to a mix tank containing 30 liters of water and then diluted to 45 liters to provide a sprayboom concentration of 0.43%, equivalent to 150 mg/m² spray coverage on the Yankee dryer at the desired component ratio. Varying the flow rates of the polymer solutions also varies the amount of solids incorporated into the base web. For instance, at 100 mg/m² spray coverage on the Yankee dryer, it is estimated that about 0.29% additive composition solids is incorporated into the tissue web. At 200 mg/m² spray coverage on the Yankee dryer, it is estimated that about 0.58% additive composition solids is incorporated into the tissue web. The sheet was dried to about 95%-98% consistency as it traveled on the Yankee dryer and to the creping blade. The creping blade subsequently scraped the tissue sheet and a portion of the additive composition off of the Yankee dryer. The creped tissue basesheet was then wound onto a core traveling at about 47 to about 52 fpm (15 mpm to 17 mpm) into soft rolls for converting. The resulting tissue basesheet had an air-dried basis weight of about 14 g/m². Two soft rolls of the creped tissue were then rewound, calendared, and plied together so that both creped sides were on the outside of the 2-ply structure. Mechanical crimping on the edges of the structure held the plies together. The plied sheet was then slit on the edges to a standard width of approximately 8.5 inches and folded, and cut to facial tissue length. Tissue samples were conditioned and tested. Table 1, below, describes the various sample codes prepared according to the present example.

TABLE 1

| Sample Code | Water-Soluble Adhesive Component | Water-Soluble Modifier Component | Bacteriostatic Component | Total Add-on Rate (mg/m² of dryer surface) |
|---|---|---|---|---|
| Control | PVA (92%) | Kymene™ (8%) | — | 16 |
| 1 | L7170 (60%) | Carbowax PEG 8000 (10%) | Merquat® 100 (30%) | 150 |
| 2 | L7170 (45%) | Carbowax PEG 8000 (10%) | Merquat® 100 (45%) | 150 |
| 3 | L7170 (60%) | Carbowax PEG 8000 (20%) | Merquat® 100 (20%) | 150 |

The tissue products were cut into two identical pieces and then placed into the sample cell and the zeta potential was measured as described above. The results are summarized in the table below.

TABLE 2

| Sample Code | Streaming Zeta Potential (mV) | Std-Dev (mv) |
|---|---|---|
| Control | +1232 | ±72 |
| 1 | +7361 | ±225 |
| 2 | +6948 | ±129 |
| 3 | +6824 | ±228 |

As can be seen from the data, the zeta potential for control was positive, but significantly lower than the zeta potential for sheets made according to the present disclosure. Without being bound by any theory, it is believed that the significant increase in zeta potential results in higher affinity for negatively charged matter, such as bacteria, thus the improved removal, capture and retention of bacteria observed in sheets made according to the present disclosure.

The tissue products were also subjected to testing to evaluate bacteria removal, capture and retention, as described above. The results are summarized in the table below.

TABLE 3

| Sample Code | Removal Efficiency | Capture Efficiency | Transfer Efficiency |
|---|---|---|---|
| Control | 84.4% | 86.7% | 3.19% |
| 1 | 98.4% | 99.9% | 0.09% |
| 2 | 97.5% | 99.9% | 0.04% |
| 3 | 94.4% | 99.9% | 0.57% |

These and other modifications and variations to the present disclosure may be practiced by those of ordinary skill in the art, without departing from the spirit and scope of the present disclosure, which is more particularly set forth in the appended claims. In addition, it should be understood that the aspects of the various embodiments may be interchanged either in whole or in part. Furthermore, those of ordinary skill in the art will appreciate that the foregoing description is by way of example only, and is not intended to limit the invention further described in the appended claims.

We claim:

1. A creped tissue product comprising:
   a. a creped tissue web having a first side and a second side;
   b. an additive composition comprising a cationic polymer having a charge density of at least about 4 equivalents of nitrogen per kilogram present on the surface of at least the first side of the creped tissue web; and wherein the product has a surface charge of at least 2000 mV.

2. The tissue product of claim 1, wherein the cationic polymer is selected from the group consisting of polyquaternium-68, polyquaternium-44, polyquaternium-46, polyquaternium-39, polyquaternium-16 and polyquaternium-11, polyquaternium-7, and polyquaternium-6.

3. The tissue product of claim 1, wherein the cationic polymer comprises polyquaternium-6.

4. The tissue product of claim 1, wherein the additive composition further comprises a water-soluble adhesive component.

5. The tissue product of claim 4, wherein the water-soluble adhesive component is the polymerization product of a cationic acrylate or methacrylate and one or more alkyl acrylates or methacrylates having the generic structure:

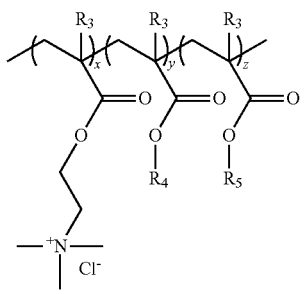

wherein x=1 to about 15 mol %; y=about 60 to about 99 mol %; and z=0 to about 30 mol %; $R_4$ is selected from methyl and ethyl; $R_5$ is selected from hydrogen, methyl, ethyl, butyl, ethylhexyl, decyl, dodecyl, hydroxyethyl, hydroxypropyl, polyoxyethylene, and polyoxypropylene.

6. The tissue product of claim 1, wherein the additive composition further comprises a water-soluble modifier component selected from the group consisting of polyethylene glycols, amine terminated ethylene glycols, and ethylene glycol-propylene glycol block copolymers.

7. The tissue product of claim 1, wherein the tissue web comprises a single ply tissue sheet containing cellulosic fibers.

8. The tissue product of claim 1, wherein the tissue web comprises multiple plies.

9. The tissue product of claim 1, wherein the tissue web has a bacteria removal efficiency of at least 95%.

10. The tissue product of claim 1, wherein the tissue web has a bacteria capture efficiency of at least 98%.

11. The tissue product of claim 1, wherein the tissue web comprises, by weight, from about 0.3% to about 3% of the additive composition.

12. A creped tissue web comprising a tissue web having a first side and a second side, the tissue web having been creped from a drum dryer to which a creping additive composition has been applied, the creping additive comprising a bacteriostatic component, a water-soluble adhesive component and a water-soluble modifier component; wherein the web has a surface charge of at least 2000 mV.

13. The creped tissue web of claim 12, wherein the bacteriostatic component comprises a water-soluble cationic polymer having a charge density of at least about 4 equivalents of nitrogen per kilogram.

14. A bacteriostatic product comprising:
   a. a tissue sheet having a first side and a second side; and
   b. a bacteriostatic composition comprising a cationic polymer having a charge density of at least 4 equivalents of nitrogen per kilogram present on the surface of at least the first side of the tissue sheet; wherein the product has a surface charge of at least 2000 mV and a bacteria capture efficiency of at least 98%.

15. The bacteriostatic product of claim 14, wherein the first side of the tissue sheet is contacted with a creping surface to apply the bacteriostatic composition to the first side of the tissue sheet.

16. The bacteriostatic product of claim 14, wherein the product has a bacteria removal efficiency of at least 95%.

17. The bacteriostatic product of claim 14, wherein the cationic polymer is selected from the group consisting of polyquaternium-68, polyquaternium-44, polyquaternium-46, polyquaternium-39, polyquaternium-16 and polyquaternium-11, polyquaternium-7, and polyquaternium-6.

18. A process for producing a sheet product comprising:
   a. applying a creping additive composition comprising a cationic polymer having a charge density of at least about 4 equivalents of nitrogen per kilogram to a moving creping surface;
   b. pressing a base sheet against the creping surface after the additive composition has been applied; and
   c. removing the base sheet from the creping surface; wherein the resulting sheet product has a surface charge of at least 2000 mV.

19. The process of claim 18, wherein the removing step comprises creping the base sheet from the creping surface using a creping blade.

20. The process of claim 18, wherein the additive composition transfers to the base sheet such that the resulting sheet comprises, by weight, from about 0.3% to about 3% additive composition.

21. The process of claim 18, wherein the base sheet comprises a wet laid tissue web.

22. The process of claim 18, wherein the base sheet comprises an air formed web.

23. The process of claim 18, wherein the base web comprises a spunbond web or a meltblown web.

24. The process of claim 18, wherein the base sheet comprises a hydroentangled web, the base sheet containing synthetic fibers and cellulosic fibers.

25. The process of claim 18, wherein the base sheet comprise a co-formed web, the web containing synthetic fibers and cellulosic fibers.

26. The process of claim 18, wherein the base sheet has a consistency of from about 10% to about 70% when pressed against the creping surface.

27. The process of claim 18, wherein the base sheet contains moisture in an amount less than 5% by weight when pressed against the creping surface.

28. The process of claim 18, wherein the creping surface is heated to a temperature from about 120° C. to about 150° C.

* * * * *